(12) United States Patent
Peter

(10) Patent No.: US 7,638,898 B2
(45) Date of Patent: *Dec. 29, 2009

(54) POWER SUPPLY FOR A COCHLEAR IMPLANT

(75) Inventor: Seligman Peter, Essendon (AU)

(73) Assignee: Cochlear Limited, Lane Cove (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/645,729

(22) Filed: Dec. 27, 2006

(65) Prior Publication Data

US 2007/0104342 A1    May 10, 2007

Related U.S. Application Data

(63) Continuation of application No. 10/250,705, filed as application No. PCT/AU02/00074 on Jan. 24, 2002, now Pat. No. 7,157,808.

(30) Foreign Application Priority Data

Jan. 24, 2001    (AU) .................................. PR 2693

(51) Int. Cl.
  H02J 1/00    (2006.01)
  H02J 1/10    (2006.01)
  H02J 7/34    (2006.01)
(52) U.S. Cl. .............................. 307/48; 307/64; 307/66; 307/71; 307/86
(58) Field of Classification Search .................... 307/48, 307/130, 66; 607/57
See application file for complete search history.

(56) References Cited

U.S. PATENT DOCUMENTS

| 3,930,192 | A |   | 12/1975 | Dinkler |
| 4,081,738 | A |   | 3/1978  | Roller |
| 4,315,162 | A |   | 2/1982  | Ferguson |
| 4,509,193 | A |   | 4/1985  | Carlson |
| 4,532,930 | A |   | 8/1985  | Crosby et al. |
| 4,563,621 | A |   | 1/1986  | Moore |
| 4,955,729 | A |   | 9/1990  | Marx |
| 5,003,244 | A | * | 3/1991  | Davis, Jr. ................. 320/119 |
| 5,355,071 | A |   | 10/1994 | Ishida et al. |

(Continued)

FOREIGN PATENT DOCUMENTS

WO    WO 96/27932    9/1996

(Continued)

OTHER PUBLICATIONS

International Search Report of PCT/AU02/00074, dated Mar. 12, 2002.

(Continued)

*Primary Examiner*—Stephen W Jackson
*Assistant Examiner*—Adi Amrany
(74) *Attorney, Agent, or Firm*—Connolly Bove Lodge & Hutz LLP

(57) ABSTRACT

A power supply for use with a tissue stimulating prosthesis, such as a cochlear implant. The power supply system comprises a first battery cell, a second battery cell, at least a third battery cell and a switch. The first and second battery cells are electrically connected in series to provide power to components of the prosthesis, while the third battery cell is configured to be selectively electrically connected in parallel with either the first or second battery cells.

34 Claims, 10 Drawing Sheets

U.S. PATENT DOCUMENTS

| | | | | |
|---|---|---|---|---|
| 5,687,129 | A | | 11/1997 | Kim |
| 5,696,833 | A | | 12/1997 | Matsen et al. |
| 5,710,504 | A | * | 1/1998 | Pascual et al. ............. 180/65.8 |
| 5,742,150 | A | * | 4/1998 | Khuwatsamrit ............. 320/116 |
| 5,747,966 | A | | 5/1998 | Minamoto |
| 5,876,425 | A | | 3/1999 | Gord et al. |
| 5,956,241 | A | | 9/1999 | LoCascio |
| 6,031,355 | A | * | 2/2000 | Rich .......................... 320/117 |
| 6,222,344 | B1 | * | 4/2001 | Peterson et al. ............. 320/119 |
| 6,518,725 | B2 | * | 2/2003 | Marten ....................... 320/116 |
| 6,815,931 | B1 | * | 11/2004 | Wells et al. ................. 320/164 |
| 6,879,855 | B2 | | 4/2005 | Schulman et al. |
| 7,378,818 | B2 | * | 5/2008 | Fowler et al. ............... 320/119 |
| 7,409,068 | B2 | * | 8/2008 | Ryan et al. ................. 381/313 |
| 2002/0109482 | A1 | * | 8/2002 | Anzawa et al. .............. 320/119 |
| 2003/0139888 | A1 | * | 7/2003 | Burns ......................... 702/63 |
| 2004/0113586 | A1 | * | 6/2004 | Chen .......................... 320/118 |
| 2005/0140335 | A1 | * | 6/2005 | Lee et al. .................... 320/118 |
| 2006/0100674 | A1 | * | 5/2006 | Molin ......................... 607/60 |
| 2007/0097719 | A1 | * | 5/2007 | Parramon et al. ............. 363/72 |

FOREIGN PATENT DOCUMENTS

WO    WO 02/060029    8/2002

OTHER PUBLICATIONS

International Preliminary Examination Report of PCT/AU02/00074 dated Sep. 18, 2002.

* cited by examiner

SIX PAIRS OF RAYOVAC CELLS

PRESENT INVENTION vs. 2 CELLS

LIMITING CURRENT vs. mA HOURS

% DUTY OF CELL1

POWER SUPPLY FOR A COCHLEAR IMPLANT

CROSS-REFERENCE TO RELATED APPLICATIONS

This application is a continuation of U.S. patent application Ser. No. 10/250,705 filed on Jul. 7, 2003, entitled, "Power Supply for a Cochlear Implant," now issued as U.S. Pat. No. 7,157,808, which is a National Stage application of International Application PCT/AU2002/000074 filed on Jan. 24, 2002, entitled "Power Supply for a Cochlear Implant," and which claims priority to Australian Patent Application PR 2693, entitled "Power Supply for a Cochlear Implant," which was filed on Jan. 24, 2001. These above documents are hereby incorporated by reference herein.

BACKGROUND

1. Field of the Invention

The present invention relates generally to electronic devices, and more particularly, to a power supply for an electronic device.

2. Related Art

Hearing impairment, which may be due to many different causes, is generally of two types, conductive or sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of these mechanisms for naturally generating nerve impulses from sound.

It is for this purpose that one type of auditory prosthesis, a Cochlear™ implant (also commonly referred to as Cochlear™ prostheses, Cochlear™ devices, Cochlear™ implant devices, Cochlear™ implant systems and the like; generally and collectively sometimes referred to herein as "cochlear implants") has been developed. As described in more detail below, cochlear implants often include an external component coupled to an internal component via a transcutaneous link. The internal component typically includes an array of stimulation electrodes implanted in the cochlea of the patient (referred to herein as a recipient). The electrode array is controlled by an electronic system encased in a hermetically sealed, biocompatible housing typically implanted in the mastoid. The electronic system, commonly referred to as a stimulator unit, essentially contains decoder and driver circuits for the stimulation electrodes. Acoustic sound reception and conversion of acoustic signals into electrical signals typically occurs in a speech processor. The speech processor may be worn by the recipient or may be implanted in the recipient. A microphone is located outside of the recipient's body, typically in a behind-the-ear housing worn on the auricle. Such a cochlear implant bypasses the hair cells in the cochlea by directly delivering electrical stimulation to the auditory nerve fibers via the implanted electrode array. This enables the brain to perceive a hearing sensation resembling the natural hearing sensation normally delivered to the auditory nerve.

Like other electrically powered devices (simply electronic devices herein), components of a cochlear implant each require a certain necessary amount of power so as to perform various operations. This necessary amount of power is typically supplied by a power supply comprising one or more battery cells. The power supply is integrated with, or electrically coupled to, the cochlear implant.

The amount of necessary power that a power supply must provide to the components of the cochlear for proper operation may vary considerably from user to user, and from operation to operation. For example, the amount of power required by components of the implant may depend on a number of factors, such as the stimulation rate employed by the implant to stimulate the cochlea or the speech processing strategy employed to convert a received sound to an electrical signal. As would be appreciated, higher stimulation rates and more complicated speech processing strategies require larger amounts of power.

Similarly, the power requirements are also strongly influenced by recipient characteristics, such as the thickness of the skin separating the elements of the external and internal components that comprise the transcutaneous link. Larger skin flaps require larger amounts of power to transmit information and power there through.

As such, a power supply employed in a cochlear implant should be designed to supply various amounts of power so that the power supply does not need to be customized based on recipient characteristics, or on the device capabilities. However, with the introduction of new technologies, the size of cochlear implants, and particularly the size of the external components, is rapidly being reduced. These reduced sizes lead to restrictions in the type, size and dimension of the power supplies which may be utilized in cochlear implants.

SUMMARY

According to a first aspect of the present invention, a cochlear implant system having internal and external components is provided. The cochlear implant system comprises: first and second battery cells electrically connected in series to supply power to the components; at least one additional battery cell; and a switch configured to electrically connect the at least one additional battery cell in parallel with one of the first or second battery cells, wherein the switch is configured to connect the additional battery cell in parallel with whichever of the first or second battery cells has a lower voltage.

According to a second aspect of the present invention, a power supply system for an electronic device comprising one or more tissue-stimulating elements is provided. The power supply system comprises: first and second battery cells electrically connected in series to supply power to one or more components of the device at least one additional battery cell; and a switch configured to electrically connect the at least one additional battery cell in parallel with one of the first or second battery cells, wherein the switch is configured to connect the additional battery cell in parallel with whichever of the first or second battery cells has a lower voltage.

According to a third aspect of the present invention, a method for supplying power to a tissue-stimulating prosthesis from a power supply is provided. The method comprises: electrically connecting the first and second battery cells in series to supply the power; comparing the voltages of the first and second battery cells; and electrically connecting the third battery cell in parallel with whichever of the first or second battery cells has a lower voltage.

According to a fourth aspect of the present invention, a cochlear implant having an internal component and an external component is provided. The cochlear implant comprises: first and second battery cells electrically connected in series to supply power to one or more of the components; at least one additional battery cell; and a switch configured to electrically connect the at least one additional battery cell in parallel with one of the first or second battery cells, wherein the switch connects the additional battery cell in parallel with whichever of the first or second battery cells has a voltage which is lower than a predetermined threshold voltage.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a power supply for an electronic device. The power supply comprises a plurality of selectively electrically connectable battery cells configured to supply power to one or more components of the electronic device. The power supply comprises first and second battery cells electrically connected in series to supply the necessary power to the device components, and a switch arrangement. The switch arrangement is configured to electrically connect a third battery cell in parallel with one of the first or second battery cells. the third battery cell is electrically connected in parallel with whichever of the first and second battery cells is exhibiting worse performance. The electrically connected first, second and third battery cells collectively supply power to the device components.

A power supply in accordance with embodiments of the present invention may be used to supply power to various types of electronic devices. For example, embodiments of the present invention may be used to provide power to a medical prostheses, such as a tissue-stimulating prosthesis. Embodiments of the present invention will be discussed herein with reference to one specific type of tissue-stimulating prosthesis, referred to herein as a cochlear implant system, or simply cochlear implant.

Figure 1:
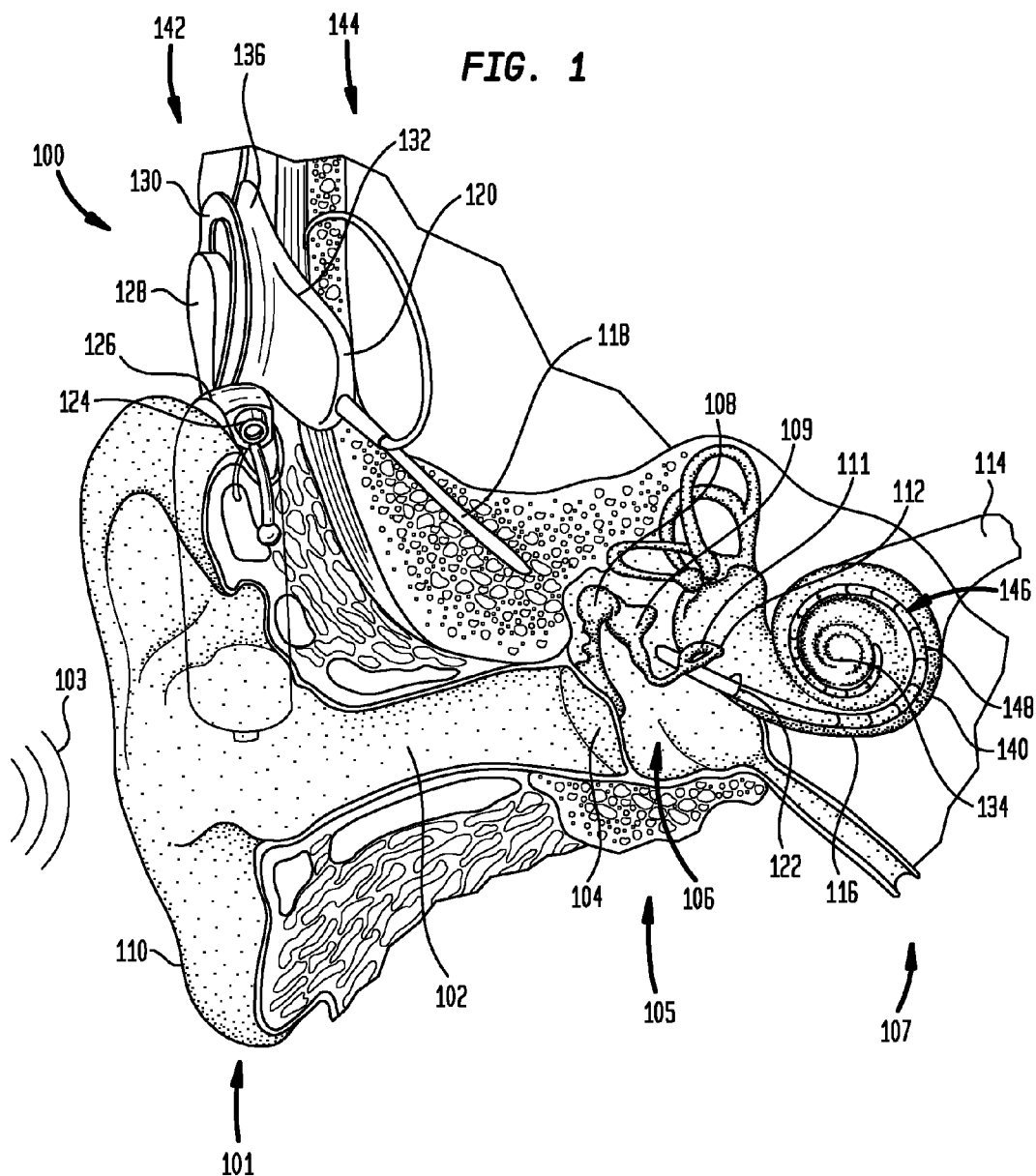
FIG. 1 is a perspective view of an exemplary medical prosthesis, a cochlear implant, in which embodiments of the present invention may be advantageously implemented.

FIG. 1 is perspective view of one embodiment of a cochlear implant 100 in which embodiments of the present invention may be advantageously implemented. The relevant components of outer ear 101, middle ear 105 and inner ear 107 are described next below. Outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate. Such vibration sets up waves of fluid motion within cochlea 140. Such fluid motion, in turn, activates tiny hair cells (not shown) that line the inside of cochlea 140. Activation of the hair cells causes appropriate nerve impulses to be transferred through the spiral ganglion cells and auditory nerve 114 to the brain, where they are perceived as sound.

Cochlear implant 100 comprises external component 142 which is directly or indirectly attached to the body of the recipient, and an internal component 144 which is temporarily or permanently implanted in the recipient. External component 142 may comprise a microphone 124 for detecting sound, an external housing 126 having speech processing elements therein, and an external transmitter unit 128. As described in more detail below, a power supply (not shown) in accordance with embodiments of the present invention may also be included in external component 142.

As shown in FIG. 1, external transmitter unit 128 comprises an external coil 130 and, preferably, a magnet (not shown) secured directly or indirectly to external coil 130. The speech processing elements within housing 126 are configured to process the output of microphone 124 that is positioned, in the depicted embodiment, on auricle 110 of the recipient. The speech processing elements generate coded signals, referred to herein as a stimulation data signals, which are provided to external transmitter unit 128 via a cable (not shown). As discussed in more detail below, the power supply of external component 142 is configured to supply necessary power to other components of cochlear implant 100.

Internal component 144 comprises an internal receiver unit 132, a stimulator unit 120, and an elongate electrode carrier 118. Internal receiver unit 132 comprises an internal transcutaneous transfer coil 136, and preferably, a magnet (also not shown) fixed relative to the internal coil. Internal receiver unit 132 and stimulator unit 120 are hermetically sealed within a biocompatible housing. Internal coil 136 receives power and stimulation data from external coil 130, as noted above. Elongate electrode carrier 118 has a proximal end connected to stimulator unit 120 and extends from stimulator unit 120 to cochlea 140. Electrode carrier 118 is implanted into cochlea 104 via a cochleostomy 122.

Electrode carrier 118 comprises an electrode array 146 disposed at the distal end thereof. Electrode array 146 comprises a plurality of longitudinally-aligned electrodes 148. Stimulation signals generated by stimulator unit 120 are applied by electrodes 148 to cochlear 140, thereby stimulating auditory nerve 114.

In one embodiment, external coil 130 transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 may be positioned in a recess of the temporal bone adjacent auricle 101 of the recipient.

Figure 2:
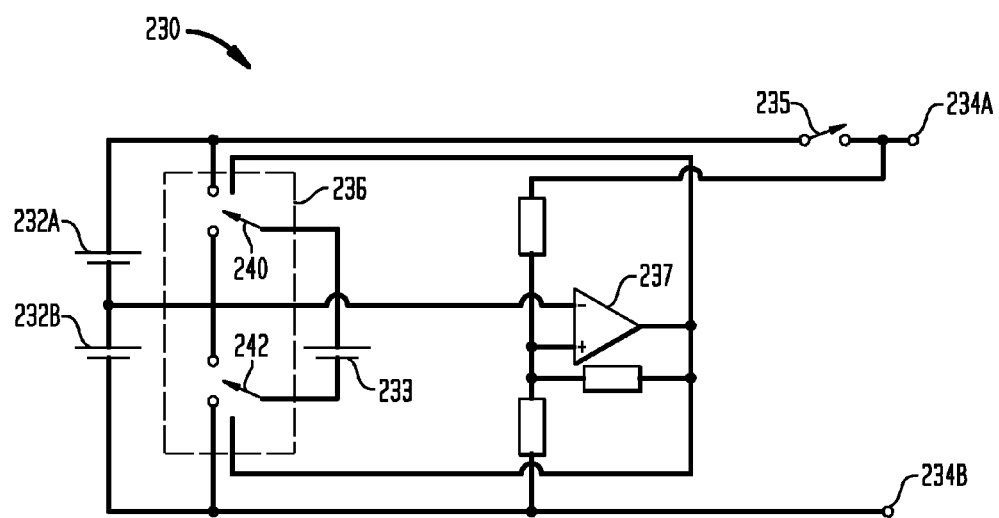
FIG. 2 is a schematic view of a power supply in accordance with embodiments of the present invention.

FIG. 2 is a schematic view illustrating the circuit layout of a power supply 230 in accordance with embodiments of the present invention. Power supply 230 may be configures for use with, for example, cochlear implant 100. As shown, power supply 230 comprises a first battery cell 232A and a second battery cell 232B electrically connected in series. In a first arrangement, electrically connected battery cells 232 are configured to supply power to one or more components of cochlear implant 100.

Power supply 230 further includes at least one additional battery cell 233, (sometimes referred to herein as "third battery cell"). As shown in FIG. 2, power supply 230 comprises a single additional battery cell 233. As discussed in more detail below, in other embodiments of the present invention, power supply 230 may comprise a plurality of additional battery cells 233.

As discussed below in more detail, third battery cell 233 is configured to be electrically connected in parallel with whichever of first or second battery cells 232 is determined to be exhibiting worse performance. Third battery cell 233 may be electrically connectable in parallel with either first or second battery cell 232 via a switch 236. In embodiments of the present invention, switch 236 comprises an analog changeover switch 236. Following connection of third battery cell 233 in parallel with one of first or second battery cells 232, the electrically connected first, second and third battery cells supply power to the implant components.

In certain embodiments of the present invention, the performance of battery cells 232 may be determined by comparing the voltages of battery cells 232 to one another. In these embodiments, the battery cell 232 having the lower voltage is determined to be exhibiting worse performance.

In other embodiments of the present invention, the performance of battery cells 232 may be determined by comparing the voltages of battery cells 232 to a predetermined threshold voltage. In these embodiments, if the voltage of one of battery cells 232 falls below the predetermined threshold voltage, the one battery cell is determined to be exhibiting worse performance.

In embodiments of the present invention, power supply 230 may comprise a control system to evaluate the voltages of battery cells 232. As shown in FIG. 2, the control system comprises a low power comparator 237. In these embodiments, the voltage of each of first and second battery cells 232 is provided to comparator 237. Comparator 237 then compares the voltages of first and second battery cells 232 to one another, or to a predetermined threshold voltage. If the voltage of one of battery cells 232 is lower than the voltage of the other of battery cells 232, or is below the predetermined threshold voltage, comparator 237 causes switch 236 to connect third battery cell 233 in parallel with whichever of the first or second battery cells 232 has the lower voltage. In embodiments of the present invention, a small amount of hysteresis (eg. about 4 mV) is built into comparator 237 to avoid excessive switching of switch 236.

In aspects of the present invention, third battery cell 233 may be connected in parallel with one of first or second battery cells 232 when power requirements of the implant components exceed the maximum power available from first and second series-connected battery cells 232 alone. In these embodiments, when power requirements of the implant components exceed the maximum power available from first and second series-connected battery cells 232 alone, comparator 237 determines which one of the first and second battery cells is exhibiting worse performance in one of the manners described above. Third battery cell 233 is then connected in parallel with whichever of first and second battery cells is exhibiting worse performance. The three batteries 232A, 232B and 233 collectively supply the larger amount of power to the implant components. Such embodiments ensure that power supply 230 is able to meet various power demands resulting from recipient characteristics or device requirements, such as large skin flaps, high stimulation rates or complicated speech processing strategies.

In certain embodiments of the present invention, because third battery cell 233 approximately halves the power demand of battery cell 232 with which the third battery is connected in parallel, the stored charge of the other of the first and second battery cells 232 will be reduced at a faster rate than the stored charges of the battery cells connected in parallel. Therefore, in such embodiments, to prevent an uneven depletion of batteries 232, power supply system 230 may be configured to alternate which third battery cell 233 is connected in parallel. In these embodiments, switching element 236 may be configured to alternatively connect first and second battery cells 232 in parallel with third battery cell 233 at a regular frequency to ensure that the charge stored in first and second batteries 232 is depleted approximately equally.

Power supply system 230 may be configured to alternate third battery 233 between first and second batteries 232 based on voltages measured by, for example, comparator 237.

It should be appreciated that in addition to the embodiments described above with reference to FIG. 2, embodiments of the present invention further include methods for supplying power to components of an electronic device, such as cochlear implant 100. In these embodiments, the method comprises the steps of electrically connecting first and second battery cells in series, and selectively electrically connecting a third battery cell in parallel with whichever battery of the first or second battery cells exhibits worse performance. As described above, in certain embodiments, a determination of which one of the first or second battery cells exhibits worse performance is made by comparing the voltages of the first and second batteries to one another. Also as described above, in other specific embodiments, a determination of which one of the first or second battery cells exhibits worse performance is made by comparing the voltages of the first and second battery cells to a predetermined threshold voltage.

In making the above determinations, the voltages of the battery cells may be measured by the power supply. In certain embodiments, the voltages of the first and second battery cells are measured with the third battery disconnected from each of the first and second battery cells.

Figure 3:
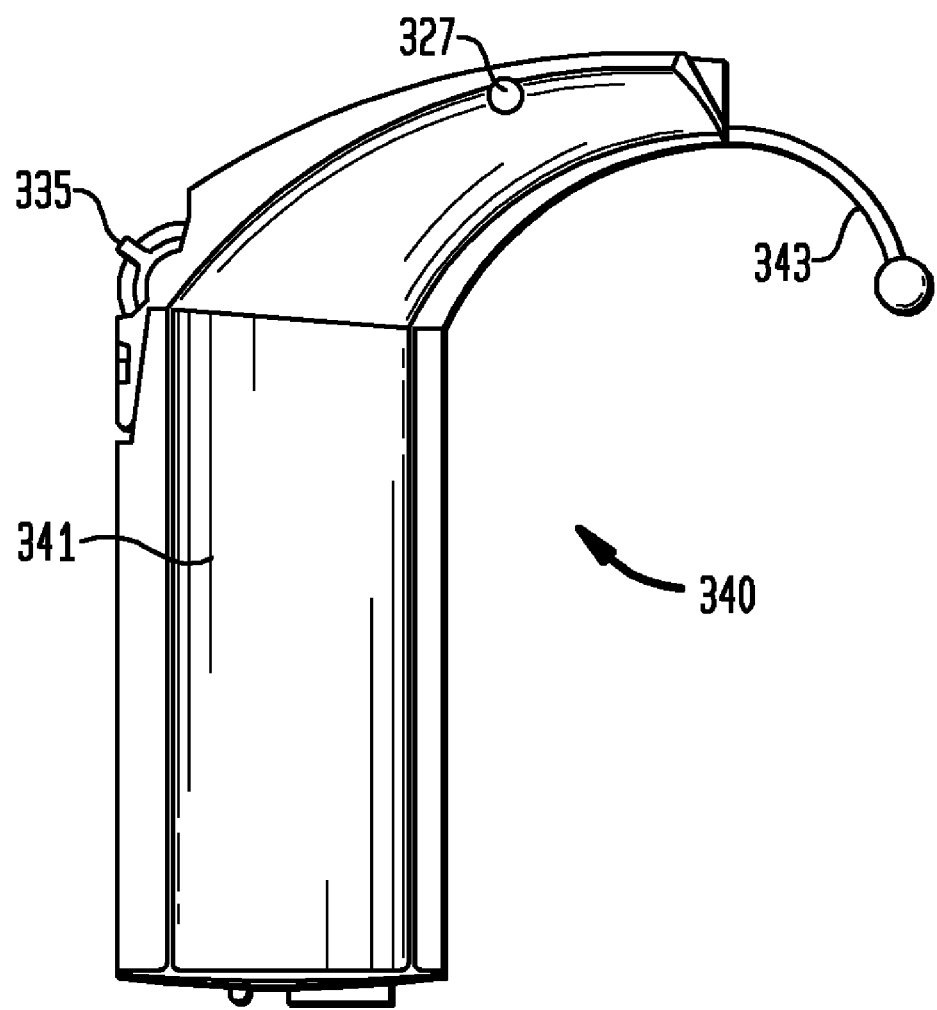
FIG. 3 is a side view of an external component of a cochlear implant in which embodiments of the present invention may be implemented.

As noted above, one example of a medical prosthesis that may be powered by power supply 230 of FIG. 2 is a tissue-stimulating cochlear implant, such as cochlear implant 100 of FIG. 1. As described with reference to FIG. 1, cochlear implant 100 may comprise an external component 142. FIG. 3 illustrates a specific embodiment of external component 142, commonly referred to as a Behind-The-Ear component (BTE) 340. BTE 340 is an external unit configured to be positioned behind-the-ear of a recipient of cochlear implant 100. BTE 340 may have therein or thereon various components of a cochlear implant 100, such as a microphone 327 and speech processing elements (not shown). As explain below, BTE 340 may further include a power supply, such as power supply 230.

Figure 4:
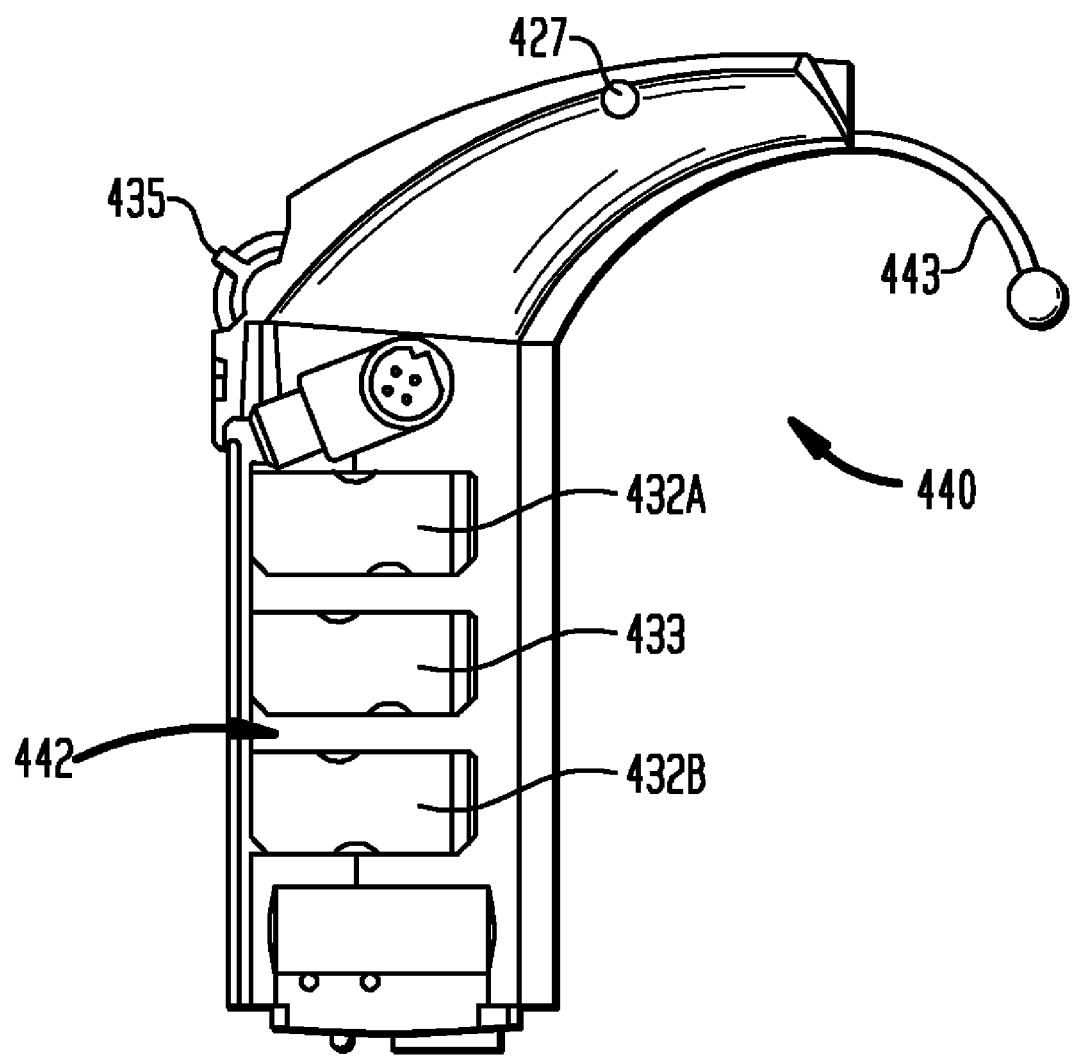
FIG. 4 is a side view of the external component of FIG. 3 having a portion of the exterior housing removed.

In the embodiment of FIG. 3, BTE 340 comprises a removable cover 341 enclosing a battery compartment (not shown). An exemplary battery compartment is illustrated in FIG. 4 as battery compartment 442. BTE 340 further comprises ear hook 343 for retaining the BTE on an auricle of the recipient, and an On/Off switch 335.

FIG. 4 illustrates an embodiment of BTE 340, referred to herein as BTE 440. In the illustrated embodiment, cover 341 has been removed to expose battery compartment 442. In the illustrated embodiment, battery compartment 442 has positioned therein a power supply comprising battery cells 432A, 432B and 433, and a switch. As shown, in a first configuration, battery cells 432A and 432B are electrically connected in series to supply power to other components of the cochlear implant, such as microphone 427, speech processing elements, the implanted electrode array, and any other electrical or electronic componentry of the cochlear implant whether it be external or internal of the body of the implantee. In a second configuration, battery cell 433 is configured to be electrically connected in parallel with one of first or second battery cells 432 in the same manner as described above with reference to FIG. 2.

Although FIG. 4 illustrates battery cells 432A, 432B and 433 mounted within a housing that also encloses other componentry of cochlear implant, it should be appreciated that in other embodiments, battery cells 432A, 432B and 433 may be mounted within a separate housing. In such exemplary embodiments, an electrical connection would be provided between the battery cells/power supply system and the other componentry of the cochlear implant.

In embodiments of the present invention, battery cells 432A, 432B and 433 may each comprise a zinc-air cell. Zinc air cells may provide several practical advantages, including a high energy density that can supply a device's requirements for a relatively long period of time relative to their size and weight. Also, zinc air cells have a relatively constant power output throughout most of their life, thereby reducing the risk of dangerous rapid discharge, such as shorting.

It should be appreciated that any suitable battery cell may be utilized in the present invention. It should also be appreciated that in certain embodiments, when mounted in a medical prosthesis, each of battery cells 432A, 432B and 433 may be surrounded by an electrically insulating material such that the battery cells are electrically insulated from each other and from the housing in which they are mounted.

In certain embodiments of the present invention, battery cells 432A, 432B and 433 are preferably all of the same design. However, in other embodiments of the present invention, one or more of battery cells 432A, 432B or 433 may be of a different design.

In certain embodiments of the present invention one or more of batteries battery cells 432A, 432B or 433 may comprise a rechargeable battery cell. In such embodiments, a power supply in accordance with embodiments of the present invention may also include one or elements to recharge the rechargeable battery cells.

Figure 5:
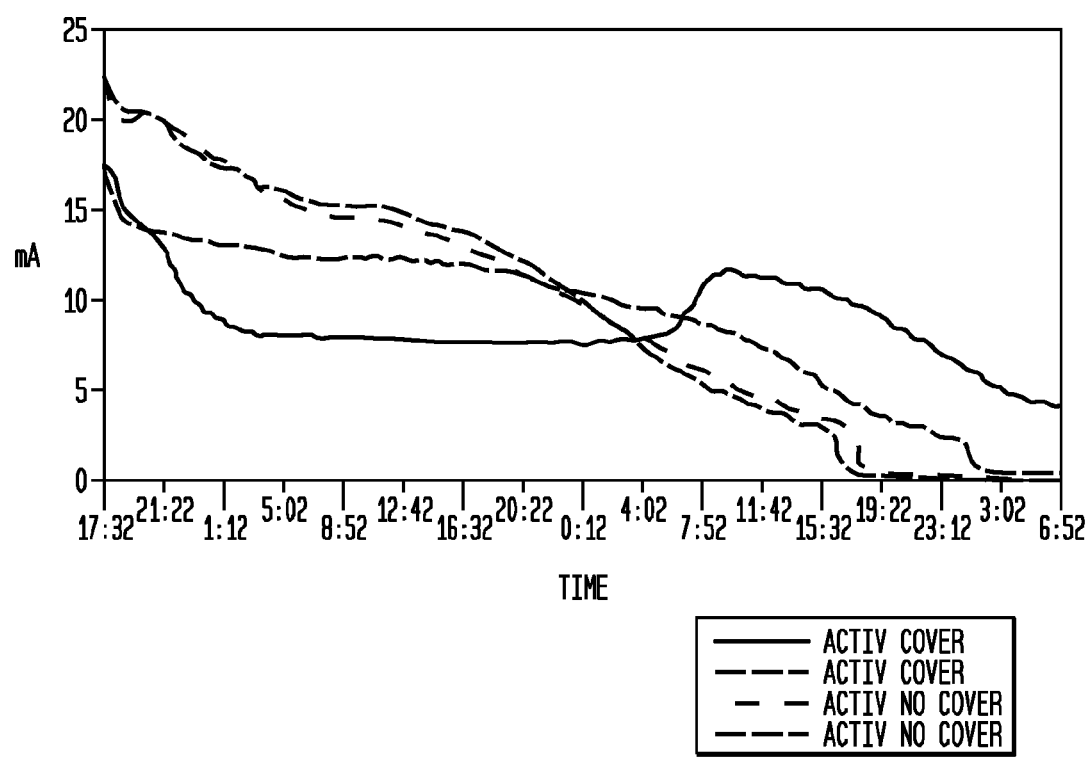
FIG. 5 is a graph illustrating typical limiting currents of four activair HPX battery cells.
Figure 6:
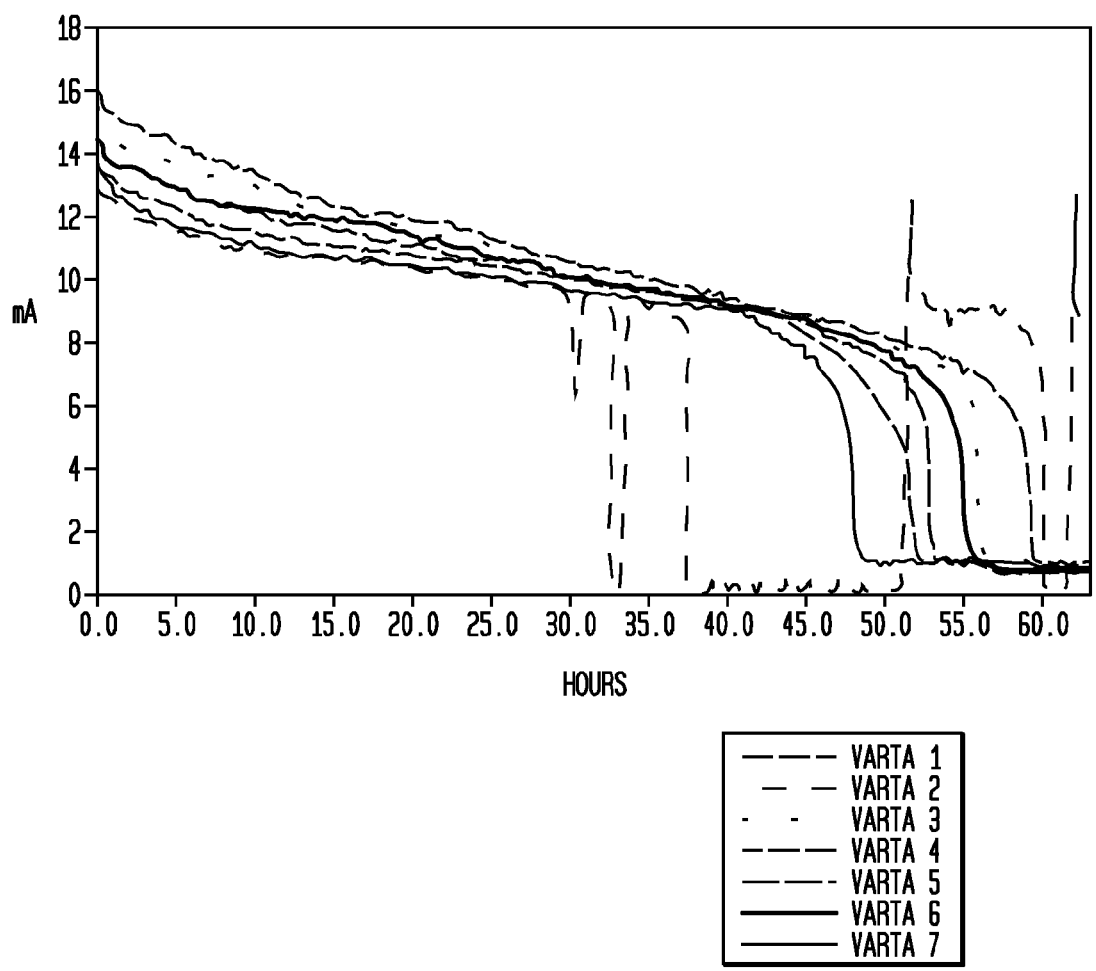
FIG. 6 is a graph illustrating limiting currents of seven VARTA® battery cells.
Figure 7:
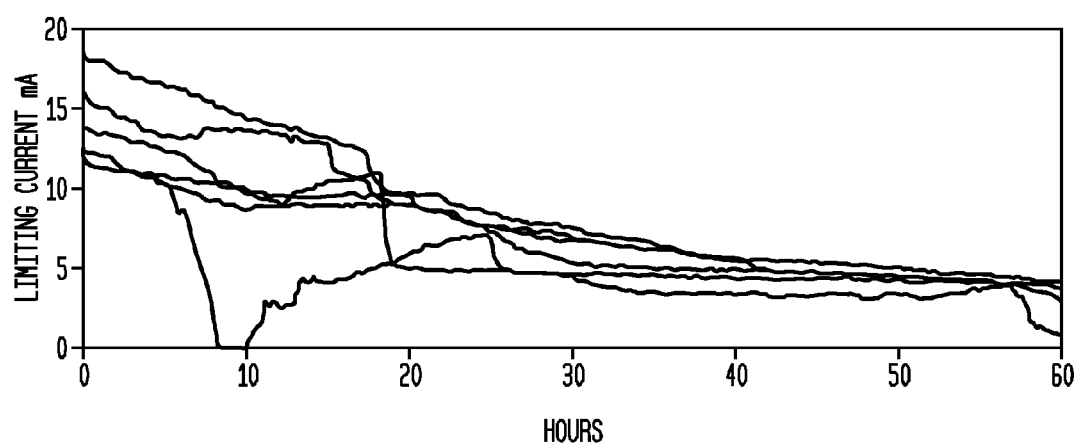
FIG. 7 is a graph illustrating limiting currents of six pairs of Rayovac® battery cells.

FIG. 5 is a graph illustrating typical limiting currents for four 675 size zinc-air Activair BPX battery cells. FIG. 5 illustrates the limiting current in mA vs. time. FIG. 6 is a graph illustrating typical limiting currents for seven 675 size zinc-air Varta® V675 battery cells, again presented as limiting current in mA vs. time. FIG. 7 is a graph illustrating the performance of six pairs of Rayovac® 675 size zinc-air cells, presented as limiting current in mA vs. time. As can be seen from FIGS. 5-7, the reliability of these cells is relatively poor, with the performance from one cell to the next being relatively inconsistent.

Figure 8:
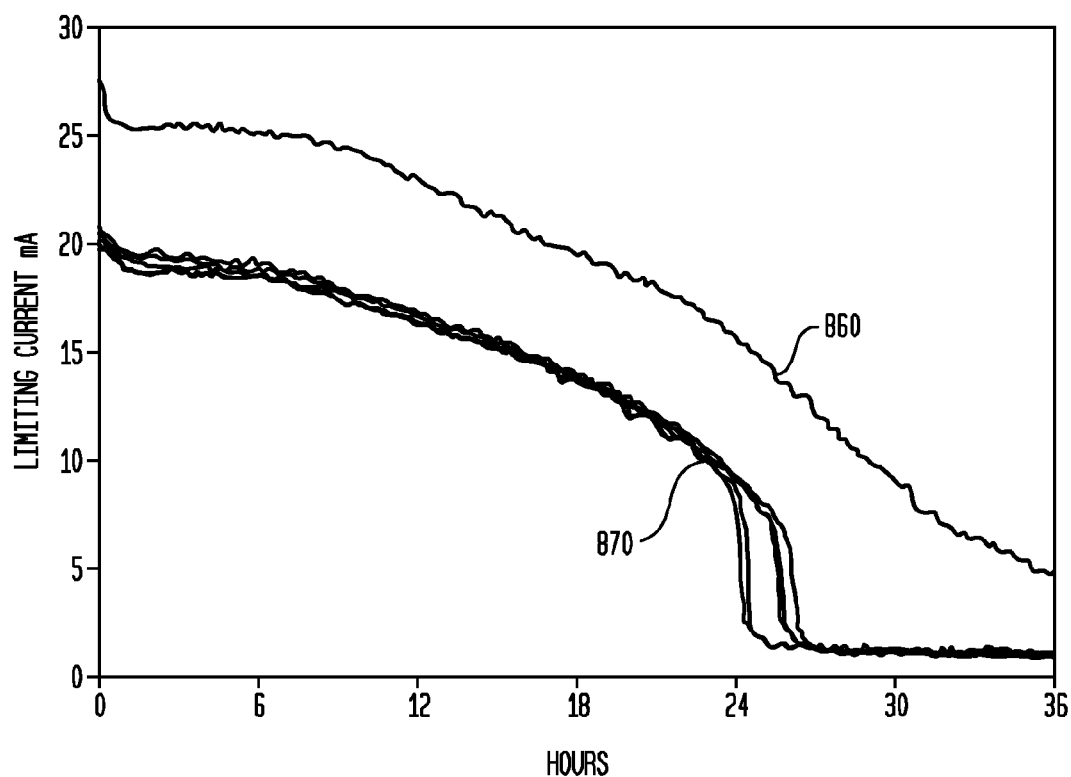
FIG. 8 is a graph illustrating the limiting current over time exhibited by a power supply in accordance with embodiments of the present invention in which three battery cells are selectively electrically connectable in series, and the limiting current over time exhibited by a two cell arrangement.
Figure 9:
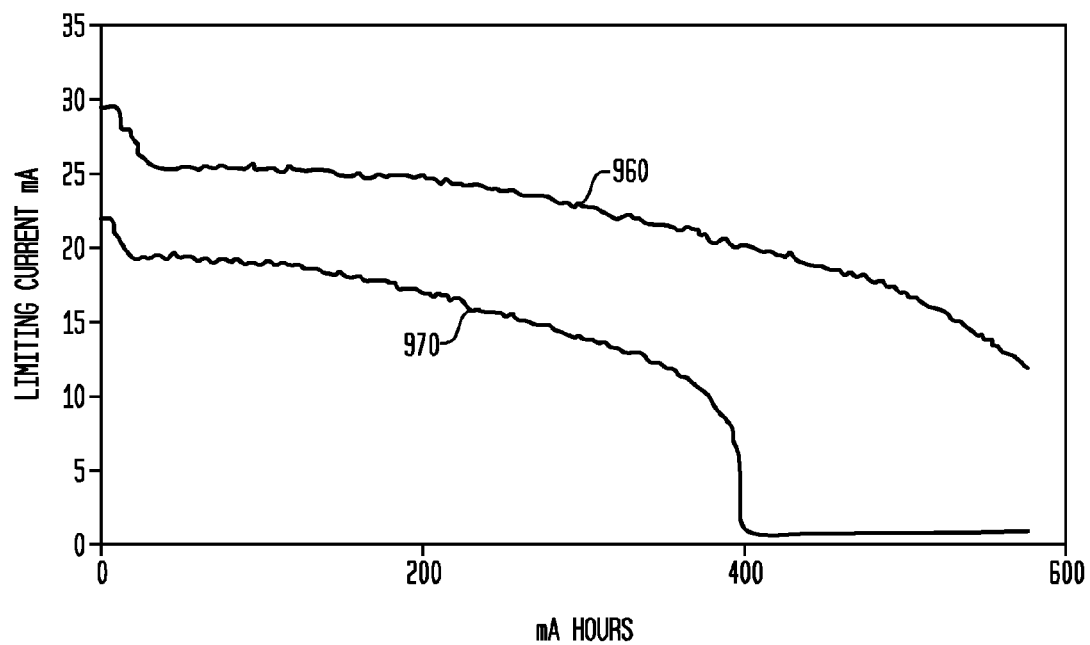
FIG. 9 is a graph illustrating the limiting current vs. mA hours in accordance with the arrangements illustrated in FIG. 8.
Figure 10:
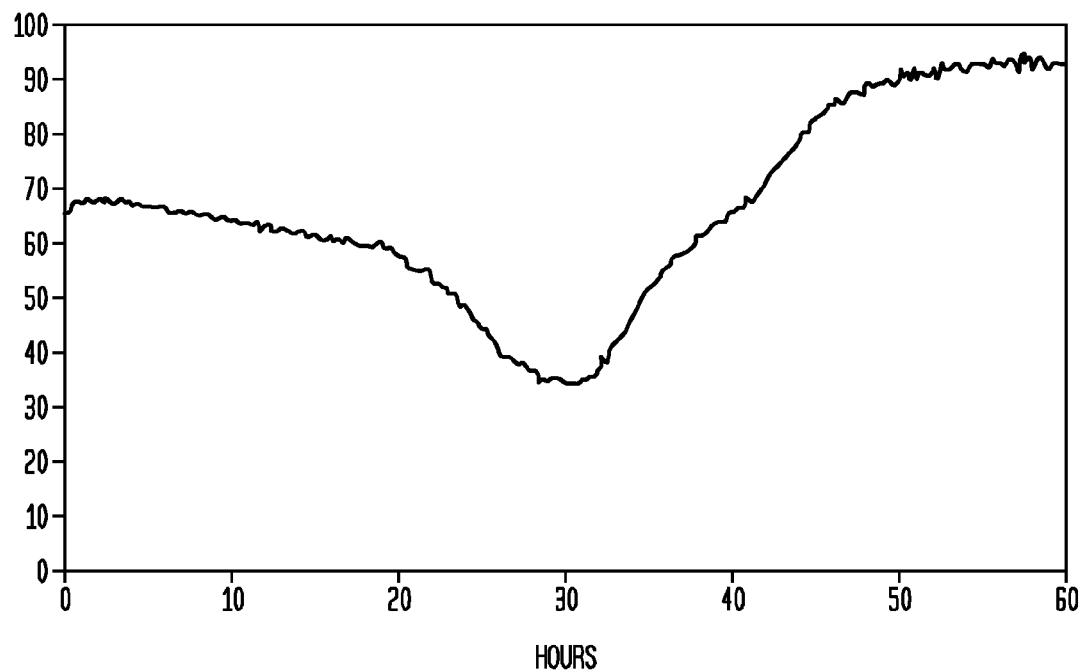
FIG. 10 is a graph illustrating the duty cycle of a battery cell utilized in embodiments of the present invention.

FIG. 8 is a graph illustrating the limiting current over time exhibited by embodiments of the present invention. Line 860 represent the limiting current vs. time for a power supply in accordance with embodiments of the present invention when loaded by a constant 2.2 Volt load. More specifically, line 860 represents the limiting current for a configuration in which two battery cells are electrically connected in series, and in which an additional battery cell is configured to be connected in parallel to one or both of the other two battery cells. Lines 870 each represent the limiting current vs. time for various two cell power supply arrangements when loaded by a constant 2.2 Volt load. As can be seen in FIG. 8, the arrangement of the present invention significantly improves the limiting current of the power supply system such that a load current can be supplied for a longer time than could be supplied by two cell power supply arrangements. This is better shown in FIG. 9, which illustrates the limiting current vs. mA hours for embodiments of the present invention and for the two cell prior art arrangement. As can be seen, for a load current of, for example, 15 mA, the available power output capacity has increased from 268 mA hours for a prior art arrangement to approximately 536 mA hours for embodiments of the present invention.

While the illustrated and described embodiments comprise two battery cells placed in series and a third battery cell configured to be electrically connectable in parallel with either of the two series-connected battery cells, it is envisaged that additional battery cells may also be used. For example, embodiments of the present invention may employ more than two battery cells in series and more than one battery cell electrically connectable in parallel with one or more of the series-connected battery cells. Such embodiments should be considered within the scope of the present invention.

Similarly, the present invention has been discussed in reference to single battery cells. However, it should be appreciated that, as used herein, each battery cell may also refer to a plurality of battery cells.

For ease of description, the present invention has been described herein with reference to one electronic device, namely a cochlear implant. However, it should be appreciated that the above described power supply may be used with other electronic devices.

Furthermore, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

The invention claimed is:

1. A cochlear implant system having an internal component and an external component, said system comprising:
   first and second battery cells electrically connected in series to supply power to said components;
   at least one additional battery cell electrically disconnected from both the first and second battery cells; and
   a switch configured to electrically connect said at least one additional battery cell in parallel with one of said first or second battery cells,
   wherein said switch is configured to connect said additional battery cell in parallel with whichever of said first or second battery cells has a lower voltage.

2. The system of claim 1, wherein said switch is configured to connect said additional battery cell in parallel with one of said first or second battery cells when the voltage of said one cell falls below the voltage of the other of said first or second battery cells by a first amount.

3. The system of claim 1, further comprising:
a low power comparator configured to compare the voltages of said first and second battery cells to determine which of said first or second battery cells has a lower voltage.

4. The system of claim 3, wherein said first and second battery cells are configured to supply a first power to one or more of said internal and external components, and wherein said comparator compares the voltages of said first and second battery cells when the power demanded by said one or more components exceeds said first power.

5. The system of claim 1, wherein at least one of said battery cells comprises a rechargeable battery cell.

6. The system of claim 5, further comprising:
an element configured to recharge said at least one rechargeable battery cell.

7. The system of claim 1, wherein said switch is configured to alternate which of said first and second battery cells is connected in parallel with said additional battery cell.

8. The system of claim 1, wherein said switch comprises an analog changeover switch.

9. The system of claim 1, wherein one or more of said battery cells comprise a zinc air cell.

10. The system of claim 1, wherein said external component comprises:
a housing; and
a speech processor,
wherein said battery cells and said speech processor are positioned in said housing.

11. The system of claim 1, wherein said external component comprises:
a first housing;
a second housing; and
a speech processor,
wherein said speech processor is positioned in said first housing, and wherein said battery cells are positioned in said second housing.

12. A power supply system for an electronic device comprising one or more tissue-stimulating elements, the system comprising:
first and second battery cells electrically connected in series to supply power to one or more components of the device;
at least one additional battery cell electrically disconnected from both the first and second battery cells; and
a switch configured to electrically connect said at least one additional battery cell in parallel with one of said first or second battery cells,
wherein said switch is configured to connect said additional battery cell in parallel with whichever of said first or second battery cells has a lower voltage.

13. The system of claim 12, wherein said switch is configured to connect said additional battery in parallel with one of said first or second battery cells when the voltage of said one cell falls below the voltage of the other of said first or second battery cells by a first amount.

14. The system of claim 12, further comprising:
a low power comparator configured to compare the voltages of said first and second battery cells to determine which of said first or second battery cells has a lower voltage.

15. The system of claim 14, wherein said first and second battery cells are configured to supply a first power to said components, and wherein said comparator compares the voltages of said first and second battery cells when the power demanded by said components exceeds said first power.

16. The system of claim 12, wherein at least one of said battery cells comprises a rechargeable battery cell.

17. The system of claim 16, further comprising:
an element configured to recharge said at least one rechargeable battery cell.

18. The system of claim 12, wherein said switch is configured to alternate which of said first and second battery cells is connected in parallel with said additional battery cell.

19. The system of claim 12, wherein said switch comprises an analog changeover switch.

20. The system of claim 12, wherein one or more of said battery cells comprise a zinc air cell.

21. A method for supplying power from a power supply to components of a tissue-stimulating prosthesis comprising first, second and third battery cells, the method comprising:
electrically connecting the first and second battery cells in series to supply said power;
comparing the voltages of the first and second battery cells;
maintaining the third battery cell electrically disconnected from the first and second battery cells; and
electrically connecting the third battery cell in parallel with whichever of the first or second battery cells has a lower voltage.

22. The method of claim 21, wherein said power supply comprises:
a low power comparator configured to compare the voltages of the first and second battery cells to determine which of said first or second cells has a lower voltage.

23. The method of claim 22, wherein said first and second battery cells are configured to supply a first power to said components, and wherein said comparator compares the voltages of said first and second battery cells when the power demanded by said components exceeds said first power.

24. The method of claim 21, wherein at least one of the battery cells comprises a rechargeable battery.

25. The method of claim 24, further comprising: recharging said at least one rechargeable battery cell.

26. The method of claim 21, further comprising:
alternating which of the first or second battery cells is connected in parallel with the third battery cell.

27. A cochlear implant having an internal component and an external component, the implant comprising:
first and second battery cells electrically connected in series to supply power to one or more of said components;
at least one additional battery cell electrically disconnected from both the first and second battery cells; and
a switch configured to electrically connect said at least one additional battery cell in parallel with one of said first or second battery cells,
wherein said switch connects said additional battery cell in parallel with whichever of said first or second battery cells has a voltage which is lower than a threshold voltage.

28. The implant of claim 27, further comprising:
a low power comparator configured to compare the voltages of said first and second battery cells to said threshold voltage.

29. The implant of claim 28, wherein said first and second battery cells are configured to supply a first amount of power to said components, and wherein said comparator compares the voltages of said first and second battery cells to said threshold voltage when the power demanded by said components exceeds said first amount of power.

30. The implant of claim 27, wherein at least one of said battery cells comprises a rechargeable battery cell.

31. The implant of claim 30, further comprising:
an element configured to recharge said at least one rechargeable battery cell.

32. The implant of claim 27, said switch is configured to alternate which of said first and second battery cells is connected in parallel with said additional battery cell.

33. The implant of claim 27, wherein said switch comprises an analog changeover switch.

34. The implant of claim 27, wherein one or more of said battery cells comprise a zinc air cell.

* * * * *